US012265760B2

(12) United States Patent
Babbush et al.

(10) Patent No.: US 12,265,760 B2
(45) Date of Patent: Apr. 1, 2025

(54) TECHNIQUES FOR OBTAINING ACCURATE DIAGONAL ELECTRONIC STRUCTURE HAMILTONIANS (71) Applicant: Google LLC, Mountain View, CA (US)

(72) Inventors: Ryan Babbush, Venice, CA (US); Jarrod Ryan McClean, Marina Del Rey, CA (US)

(73) Assignee: Google LLC, Mountain View, CA (US)

( * ) Notice: Subject to any disclaimer, the term of this patent is extended or adjusted under 35 U.S.C. 154(b) by 1073 days.

(21) Appl. No.: 16/976,229

(22) PCT Filed: Aug. 10, 2018

(86) PCT No.: PCT/US2018/046249
§ 371 (c)(1),
(2) Date: Aug. 27, 2020

(87) PCT Pub. No.: WO2019/203874
PCT Pub. Date: Oct. 24, 2019

(65) Prior Publication Data
US 2021/0035009 A1 Feb. 4, 2021

Related U.S. Application Data (60) Provisional application No. 62/660,505, filed on Apr. 20, 2018.

(51) Int. Cl.
G06F 30/20 (2020.01)
G06N 10/20 (2022.01)
(Continued)

(52) U.S. Cl.
CPC ............ G06F 30/20 (2020.01); G06N 10/20 (2022.01); G16C 10/00 (2019.02); G16C 60/00 (2019.02)

(58) Field of Classification Search
CPC .......... G06N 10/00; G16C 10/00; G16C 60/00
See application file for complete search history.

(56) References Cited

U.S. PATENT DOCUMENTS

| 2004/0000666 | A1* | 1/2004 | Lidar | H10N 69/00 257/31 |
| 2013/0144925 | A1* | 6/2013 | Macready | G06N 10/00 708/620 |

(Continued)

FOREIGN PATENT DOCUMENTS

WO    WO 2005/122052    12/2005

OTHER PUBLICATIONS

Jarrod R. McClean et al.; "The theory of variational hybrid quantum-classical algorithms"; 1Computational Research Division, Lawrence Berkeley National Laboratory, Berkeley, CA; New J. Phys. 18 (2016) 023023 (Year: 2016).*

(Continued)

Primary Examiner — Rehana Perveen
Assistant Examiner — Nupur Debnath
(74) Attorney, Agent, or Firm — Fish & Richardson P.C.

(57) ABSTRACT

Methods, systems and apparatus for simulating a physical system described by an electronic structure Hamiltonian expressed in an orthonormal basis. In one aspect, a method includes decomposing the electronic structure Hamiltonian into a sum of sub-Hamiltonians, wherein each sub-Hamiltonian in the sum of sub-Hamiltonians is expressed in one of multiple bases; simulating evolution of the physical system using the decomposed electronic structure Hamiltonian; and using the simulated evolution of the physical system using the decomposed electronic structure Hamiltonian to determine properties of the physical system.

19 Claims, 4 Drawing Sheets (51) Int. Cl.
*G16C 10/00* (2019.01)
*G16C 60/00* (2019.01)

(56) References Cited

U.S. PATENT DOCUMENTS

| | | | | |
|---|---|---|---|---|
| 2016/0283857 A1* | 9/2016 | Babbush | | G06F 15/82 |
| 2017/0177782 A1* | 6/2017 | Hastings | | G06F 30/394 |
| 2017/0330101 A1* | 11/2017 | Hastings | | G06N 99/007 |
| 2018/0096085 A1* | 4/2018 | Rubin | | G16C 10/00 |
| 2018/0232652 A1* | 8/2018 | Curtis | | G06N 10/00 |
| 2019/0095811 A1* | 3/2019 | Antonio | | G06N 10/00 |
| 2020/0265334 A1* | 8/2020 | Haider | | H01L 29/66977 |
| 2020/0293937 A1* | 9/2020 | Babbush | | G06N 10/60 |

OTHER PUBLICATIONS

David Poulin et al.; "The Trotter Step Size Required for Accurate Quantum Simulation of Quantum Chemistry"; (Year: 2014).*

Yinghua Wu et al.; "Matching-pursuit for simulations of quantum processes"; J. Chem. Phys., vol. 118, No. 15, Apr. 15, 2003 (Year: 2003).*

Nurdan Demirci Sankr; "Flexible Electronics: Materials and Device Fabrication"; Dissertation submitted to the Faculty of Virginia Polytechnic Institute and State University (Year: 2005).*

R. Barends et al.; "Digital quantum simulation of fermionic models with a superconducting circuit"; (Year: 2015).*

M. B. Hastings et al.; "Improving Quantum Algorithms for Quantum Chemistry"; (Year: 2014).*

CA Office Action in Canadian Application No. 3,093,230, dated Oct. 25, 2021, 4 pages.

Aspuru-Guzik et al., "Simulated quantum computation of molecular energies," Science, Sep. 2005, 309(5741):1704-7.

Babbush et al., "Techniques for obtaining accurate diagonal electronic structure Hamiltonians," Google Inc., Venice, CA, Jan. 2018, 3 pages.

Babbush et al., "Low depth quantum simulation of electronic structure," arXiv preprint arXiv:1706.00023, May 2017, 41 pages.

Barkoutsos et al., "Fermionic Hamiltonians for quantum simulations: a general reduction scheme," arXiv preprint arXiv:1706.03637, Jun. 2017.

Brown et al., "Using quantum computers for quantum simulation," Entropy, Nov. 2010, 12(11):2268-307.

Kassal et al., "Simulating chemistry using quantum computers," Annual review of physical chemistry, May 2011, 62:185-207.

Kivlichan et al., "Quantum Simulation of Electronic Structure with Linear Depth and Connectivity," Journal of Physics A: Mathematical and Theoretical, Nov. 2017, 8 pages.

PCT International Search Report and Written Opinion in International Appln. No. PCT/US2018/046249, dated Oct. 29, 2020, 10 pages.

Romero et al., "Strategies for quantum computing molecular energies using the unitary coupled cluster ansatz," Quantum Science and Technology, Oct. 2018, 4(1):014008.

Tropp et al., "Signal recovery from random measurements via orthogonal matching pursuit," IEEE Transactions on information theory, Dec. 2007, 53(12):4655-66.

Whitfield et al., "Simulation of electronic structure hamiltonians using quantum computers," Molecular Physics, Mar. 2011, 109(5):735-50.

Berry et al., "Efficient quantum algorithms for simulating sparse hamiltonians," Communications in Mathematical Physics, Dec. 14, 2006, 270(2):359-371.

EP Office Action in European Appln. No. 18762961.3, dated Nov. 15, 2022, 5 pages.

Kivlichan et al., "Bounding the costs of quantum simulation of many-body physics in real space" J. Phys. A: Math. Theor. 50, 2017, 32 pages.

* cited by examiner

TECHNIQUES FOR OBTAINING ACCURATE DIAGONAL ELECTRONIC STRUCTURE HAMILTONIANS

CROSS-REFERENCE TO RELATED APPLICATION

This application is a National Stage Application under 35 U.S.C. § 371 and claims the benefit of International Application No. PCT/US2018/046249, filed Aug. 10, 2018, which claims priority to U.S. Application No. 62/660,505, filed Apr. 20, 2018, the disclosure of which is incorporated herein by reference.

BACKGROUND

This specification relates to quantum computing.

Quantum simulators are devices designed to provide information and insights about physical systems or devices. Quantum simulators enable physical systems that are difficult to study in a laboratory or impossible to model using a classical processor to be simulated.

SUMMARY

This specification describes technologies for obtaining and simulating diagonal electronic structure Hamiltonians.

In general, one innovative aspect of the subject matter described in this specification can be implemented in a method for simulating a physical system described by an electronic structure Hamiltonian expressed in an orthonormal basis, the method comprising: decomposing the electronic structure Hamiltonian into a sum of sub-Hamiltonians, wherein each sub-Hamiltonian in the sum of sub-Hamiltonians is expressed in one of multiple bases; simulating evolution of the physical system using the decomposed electronic structure Hamiltonian; and using the simulated evolution of the physical system using the decomposed electronic structure Hamiltonian to determine properties of the physical system.

Other implementations of this aspect include corresponding computer systems, apparatus, and computer programs recorded on one or more computer storage devices, each configured to perform the actions of the methods. A system of one or more classical and/or quantum computers can be configured to perform particular operations or actions by virtue of having software, firmware, hardware, or a combination thereof installed on the system that in operation causes or cause the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination. In some implementations the physical system comprises a periodic physical system. In some implementations the physical system comprises a non-periodic physical system, for example a single molecule.

In some implementations the orthonormal basis comprises a Gaussian or general molecular orbital basis.

In some implementations the electronic structure Hamiltonian expressed in the orthonormal basis and the decomposed electronic structure Hamiltonian expressed in multiple bases are equivalent.

In some implementations the decomposed electronic structure Hamiltonian expressed in multiple bases approximates the electronic structure Hamiltonian expressed in the orthonormal basis.

In some implementations decomposing the electronic structure Hamiltonian into a sum of sub-Hamiltonians comprises decomposing the electronic structure Hamiltonian into a sum of sub-Hamiltonians wherein each sub-Hamiltonian comprises the product of i) a transformation operator effecting a respective basis rotation, ii) a fermionic Hamiltonian expressed in the respective basis, the fermionic Hamiltonian comprising $O(N^2)$ terms with N representing system size, and iii) a Hermitian conjugate of the transformation operator effecting the respective basis rotation.

In some implementations the fermionic Hamiltonian comprises a kinetic energy term and an interaction term.

In some implementations the fermionic Hamiltonian is given by $$H(\vec{T}_l, \vec{V}_l) = \sum_{pq} T_{l,pq} a_p^\dagger a_q + \sum_{p \neq q} V_{l,pq} n_p n_q$$

where $a_p^\dagger$, $a_q$ represent fermionic creation and annihilation operators, $n_p = a_p^\dagger a_p$ represents the number operator and $T_{l,pq}$, $V_{l,pq}$ represent scalar coefficients.

In some implementations Trotter steps under the fermionic Hamiltonian may be efficiently implemented, for example using a linear array or linear depth procedure.

In some implementations decomposing the electronic structure Hamiltonian into a sum of sub-Hamiltonians comprises: defining an initial basis and iteratively determining each sub-Hamiltonian in the sum of sub-Hamiltonians, comprising for each iteration: identifying a basis transformation that defines a basis for the iteration; determining i) a transformation operator effecting the identified basis transformation, and ii) the fermionic Hamiltonian expressed in the basis for the iteration.

In some implementations decomposing the electronic structure Hamiltonian into a sum of sub-Hamiltonians comprises: determining multiple candidate decompositions of the electronic structure Hamiltonian; and selecting a candidate decomposition comprising the fewest number of sub-Hamiltonians as the decomposition.

In some implementations selecting a candidate decomposition comprising the fewest number of sub-Hamiltonians as the decomposition comprises applying a matching pursuit algorithm.

In some implementations applying a matching pursuit algorithm comprises: set an initial residue; iteratively performing, until a termination criterion is satisfied, steps comprising: identifying a basis rotation $u_i$ and scalar coefficients $T_i$, $v_i$ that define a sub-Hamiltonian $R(u_i) H(\vec{T}_i, \vec{V}_i) R(u_i)^\dagger$ that maximizes the magnitude of the overlap with a residual for previous repetition; calculate a constant $c_i = \langle R_i \widetilde{H}_i \rangle / \| \widetilde{H}_i \|^2$; set $R_{i+1} = R_i - c_i \widetilde{H}_i$; determine whether $\|R_{i+1}\| < \epsilon$; in response to determining that $\|R_{i+1}\| \geq \epsilon$, performing a further iteration; in response to determining that $\|R_{i+1}\| < \epsilon$, terminating the performing; and setting the candidate composition as $\tilde{H} = \sum_i^L c_i \widetilde{H}_i$ where L represents the total number of iterations.

In some implementations the method further comprises performing an orthogonal matching pursuit algorithm by solving an additional linear system in each iteration that optimizes the constant $c_i$ given all current selected atoms.

In some implementations simulating evolution of the physical system using the decomposed electronic structure Hamiltonian comprises: implementing a Trotter step using a unitary operator defined as a product of terms, each term corresponding to a respective identified basis for each iteration, each term comprising a product of i) the transformation operator effecting the basis transformation for the iteration, ii) a Trotter step under the fermionic Hamiltonian expressed in the basis for the iteration, and iii) the Hermitian conjugate of the transformation operator effecting the basis transformation for the iteration.

In some implementations implementing the Trotter step using the unitary operator comprises applying a quantum circuit effecting the unitary operator on a state of a quantum system.

In some implementations implementing the Trotter step using the unitary operator comprises simulating the Trotter step.

The subject matter described in this specification can be implemented in particular ways so as to realize one or more of the following advantages The presently described disclosure represents a significant and widely applicable improvement to the state of the art in simulating quantum systems. The techniques described in this specification enable systems of practical interest to be simulated on near-term quantum devices, and reduce the expected cost for the same simulations done in an error corrected regime. This can make larger, more complex systems relevant to industrial applications to be efficiently simulated.

More specifically, a system implementing techniques for obtaining accurate diagonal electronic structure Hamiltonians, as described in this specification, can generate a compact representation of a Hamiltonian to be simulated without restricting to a special basis set. More specifically, the compact representation includes $N^2$ sub-Hamiltonians, with N representing system size, where each sub-Hamiltonian can be efficiently simulated. Therefore, the techniques described herein extend the reach of known simulation techniques.

In addition, the systems and methods described in this specification may be used to simulate a wide variety of physical systems including both periodic and non-periodic systems.

Furthermore, the techniques described in this specification provide additional benefits beyond direct Hamiltonian simulation of a quantum system. In particular, these same techniques can be used to form new, refinable, low-depth ansatzes for use in near-term variational methods. In fact, the techniques described in this specification are likely to supersede many previous low-depth ansatz works including known unitary coupled cluster techniques. In addition, the techniques described in this specification provide a systematic approximation scheme for the construction of approximate adiabatic ansatzes for variational use or otherwise. That is, at each step it may be used to provide a low-rank Hamiltonian representation that is far easier to simulate than the full Hamiltonian, but provides much of the interaction effects.

Generally, the techniques described in this specification may be applied to simulate evolution generated by general fermionic operators with 4-mode terms, such as unitary coupled clusters or other ansatz for variational techniques.

The details of one or more implementations of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Simulating the electronic structure Hamiltonian has applications in a variety of different areas ranging from pharmaceutical synthesis to the design of novel catalysts and materials. However, simulating the electronic structure Hamiltonian is highly complex due to the exponential scaling of required resources as a function of system size N.

One example approach for quantum simulation of the electronic structure Hamiltonian includes using Gaussian basis functions in the second quantization, for which the Hamiltonian contains $O(N^4)$ terms with N representing the number of spin-orbitals. Another known approach uses a careful selection of special basis functions to yield a Hamiltonian with $O(N^2)$ terms with a diagonal two-body Coulomb operator.

This specification describes improved systems and methods for simulating the electronic structure Hamiltonian. Instead of simulating the electronic structure Hamiltonian expressed in a single given basis, the electronic structure Hamiltonian is decomposed into a combination of sub-Hamiltonians. Each sub-Hamiltonian is expressed in a different basis and contains $O(N^2)$ terms. The structure of each of the $O(N^2)$ terms enables the $O(N^2)$ terms to be efficiently simulated using known simulation techniques. The systems and methods can be used to efficiently simulate both periodic and non-periodic systems within a target precision.

Example Hardware

Figure 1:
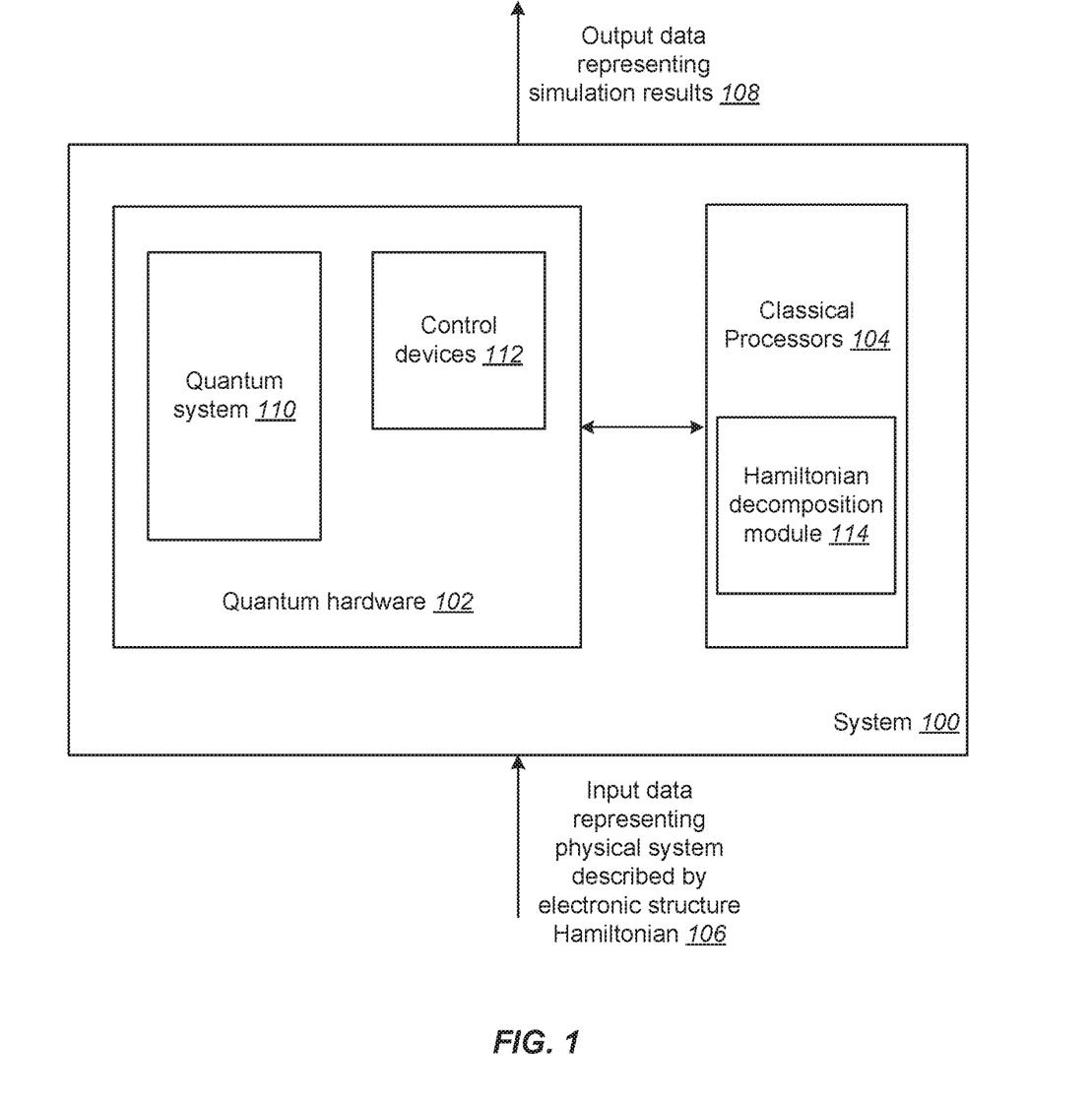
FIG. 1 depicts an example system for simulating a physical system described by an electronic structure Hamiltonian expressed in an orthonormal basis.

FIG. 1 depicts an example system 100 for simulating a physical system described by an electronic structure Hamiltonian expressed in an orthonormal basis. The example system 100 is an example of a system implemented as classical or quantum computer programs on one or more classical computers or quantum computing devices in one or more locations, in which the systems, components, and techniques described below can be implemented.

The system 100 may include quantum hardware 102 in data communication with a classical processor 104. The system 100 may receive as input data that may include data representing a physical system of interest, e.g., input data 106. The received data representing a physical system of interest may include data representing a physical system that is to be modeled or simulated. In some implementations the received data may represent a physical system that is described by an electronic structure Hamiltonian, e.g., a single molecule, material, or a chemical. The physical system may be a periodic or non-periodic system.

The system may generate as output data representing results of simulating the physical system of interest, e.g., output data 108, and may include data that may be used to determine properties of the physical system. For example, as described above, in some implementations the physical system may be a chemical. In these cases data representing simulation results may be used to determine properties of the chemical, e.g., a rate of a chemical reaction. As another example, also described above, in some implementations the physical system may be a material, e.g., a semiconductor. In these cases data representing simulation results may be used to determined properties of the material, e.g., conductivity.

The system 100 is configured to perform classical computations in combination with quantum computations using the classical processors 104 and quantum hardware 102. The quantum hardware 102 may include a quantum system 110. The quantum system 110 may include one or more multi-level quantum subsystems, e.g., qubits or audits. In some implementations the multi-level quantum subsystems may be superconducting qubits, e.g., Gmon qubits. The type of multi-level quantum subsystems that the system 100 utilizes is dependent on the physical system of interest. For example, in some cases it may be convenient to include one or more resonators attached to one or more superconducting qubits, e.g., Gmon or Xmon qubits. In other cases ion traps, photonic devices or superconducting cavities (with which states may be prepared without requiring qubits) may be used. Further examples of realizations of multi-level quantum subsystems include fluxmon qubits, silicon quantum dots or phosphorus impurity qubits. In some cases the multi-level quantum subsystems may be a part of a quantum circuit. In this case the quantum hardware 102 may include one or more control devices 112 that implement quantum logic gates on the quantum system 110.

The classical processors 104 may include a Hamiltonian decomposition module 114 that is configured to process received input data representing an electronic structure Hamiltonian, e.g., data representing an electronic structure Hamiltonian expressed in an orthonormal basis such as a Gaussian or general molecular orbital basis, to generate data representing a decomposed version of the electronic structure Hamiltonian that is equivalent to or approximates the electronic structure Hamiltonian expressed in the orthonormal basis. The decomposed version of the electronic structure Hamiltonian includes a sum of sub-Hamiltonians that are each expressed in a respective basis and that each include $O(N^2)$ terms. In some implementations generating data representing such a decomposed version of the electronic structure Hamiltonian may include applying matching pursuit algorithms and/or density fitting methods when processing the received input data. Example processes for decomposing an electronic structure Hamiltonian into a sum of sub-Hamiltonians, where each sub-Hamiltonian in the sum of sub-Hamiltonians is expressed in one of multiple bases, is described in detail below with reference to FIGS. 2-4.

The classical processors 104 may further be configured to simulate the evolution of the physical system specified by the input data 106 using a generated decomposed electronic structure Hamiltonian. For example, the classical processors 104 may be configured to simulate multiple Trotter steps under the decomposed electronic structure Hamiltonian.

Alternatively, the quantum hardware 102 may be configured to simulate the evolution of the physical system specified by the input data 106 using a generated decomposed electronic structure Hamiltonian. For example, as described in more detail below, the quantum hardware 102 may be configured to implement multiple Trotter steps by applying a quantum circuit effecting a unitary operator that is dependent on the decomposed electronic structure Hamiltonian, as described in Equation (6) below, on a state of the quantum system 110.

Programming the Hardware

Figure 2:
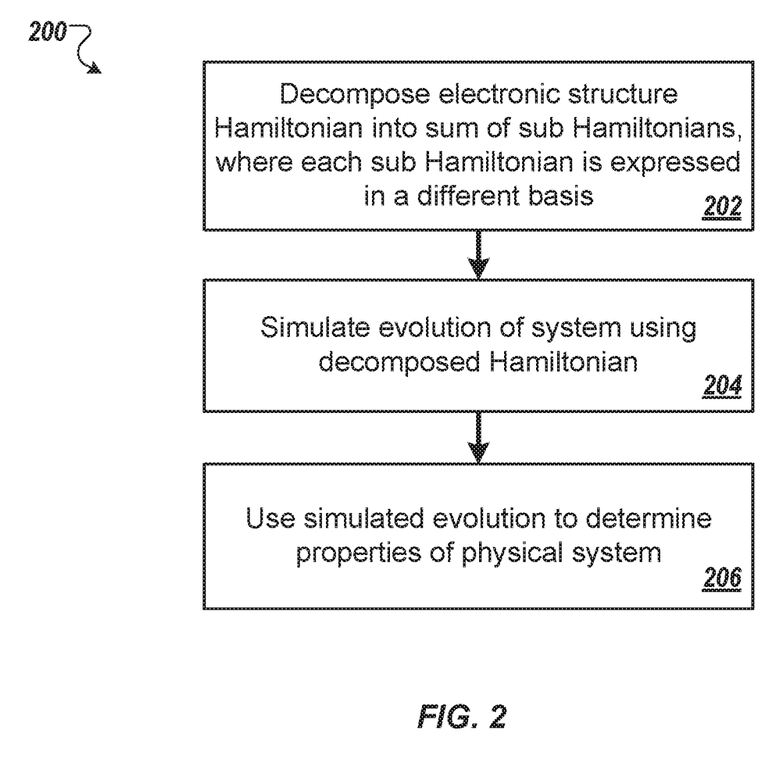
FIG. 2 is a flow diagram of an example process for simulating a physical system described by an electronic structure Hamiltonian expressed in an orthonormal basis.

FIG. 2 is a flow diagram of an example process 200 for simulating a physical system described by an electronic structure Hamiltonian expressed in an orthonormal basis. For convenience, the process 200 will be described as being performed by a system of one or more classical or quantum computing devices located in one or more locations. For example, a quantum computation system, e.g., the system 100 of FIG. 1, appropriately programmed in accordance with this specification, can perform the process 200.

The electronic structure Hamiltonian describing the physical system may be expressed in an arbitrary orthonormal basis, e.g., a Gaussian or general molecular orbital basis, and may be given by Equation (1) below.

$$\hat{H} = \sum_{p,q} h_{p,q} a_p^\dagger a_q + \frac{1}{2} \sum_{pqrs} h_{pqrs} a_p^\dagger a_q^\dagger a_r a_s. \qquad (1)$$

In Equation (1), $a_p$ and $a_p^\dagger$ represent annihilation and creation operators for spin orbital p and $h_{p,q}$, $h_{pqrs}$ represent scalar coefficients that may be given by known integrals over the basis functions dependent on the particular discretization scheme. In some implementations the electronic structure Hamiltonian may describe a periodic physical system. In other implementations the electronic structure Hamiltonian may describe a non-periodic physical system, e.g., a single molecule.

The system decomposes the electronic structure Hamiltonian into a sum of sub-Hamiltonians, wherein each sub-Hamiltonian in the sum of sub-Hamiltonians is expressed in one of multiple bases (step 202). In some cases, the electronic structure Hamiltonian described by Equation (1) above may be difficult to simulate using known techniques. For example, the electronic structure Hamiltonian may describe a non-periodic system. Matrices representing Hamiltonians (expressed in a given basis) that describe periodic systems typically comprise an underlying structure that can be used to simplify calculations associated with simulating the periodic system, e.g., repetitions in the underlying structure can be used to reduce a number of multiplication operations needed to simulate the periodic system. However, matrices representing Hamiltonians (expressed in a given basis) that describe non-periodic systems may not include such underlying structures. Efficiently simulating such systems may therefore be challenging.

However, by decomposing the electronic structure Hamiltonian (expressed in an orthonormal basis) using the below described techniques, the electronic structure Hamiltonian is mapped to a combination of Hamiltonians with a particular structure and expressed in different respective bases, where known simulation techniques can be efficiently applied.

More specifically, each sub-Hamiltonian in the sum of sub-Hamiltonians may be represented as a product of i) a transformation operator effecting a respective basis rotation, ii) a fermionic Hamiltonian expressed in the respective basis, the fermionic Hamiltonian including $O(N^2)$ terms having a particular structure (as described in more detail below with reference to Equation (5)), and iii) a Hermitian conjugate of the transformation operator effecting the respective basis rotation. For example, the decomposed electronic structure Hamiltonian may be given by Equation (2) below.

$$\tilde{H} = \sum_{l=1}^{L} R(u_l) H(\vec{T}_l, \vec{V}_l) R(u_l)^\dagger. \quad (2)$$

In Equation (2), $R(u_l)$ represents the transformation operator, given by Equation (3) below, effecting an arbitrary basis rotation given by Equation (4) below.

$$R(u) = \exp\left(\sum_{p,q} [\log u]_{pq} (a_p^\dagger a_q - a_q^\dagger a_p)\right) \quad (3)$$

$$\tilde{a}_p^\dagger = \sum_q a_q^\dagger u_{pq} \quad \tilde{a}_p = \sum_q a_p u_{pq}^*. \quad (4)$$

In Equations (3) and (4), u represents an N by N matrix that completely specifies the basis transformation between two sets of N spin-orbitals. The transformation operator R(u) may be implemented with gate depth N on a linear array using known techniques for simulating an electronic structure with linear depth and connectivity.

In Equation (2), $H(\vec{T}_l, \vec{V}_l)$ represents the fermionic Hamiltonian expressed in a basis defined by the basis transformation $u_l$. More specifically, the fermionic Hamiltonian expressed in a basis defined by the basis transformation $u_l$ may be given by Equation (5) below.

$$H(\vec{T}_l, \vec{V}_l) = \sum_{pq} T_{l,pq} a_p^\dagger a_q + \sum_{p \neq q} V_{l,pq} n_p n_q. \quad (5)$$

In Equation (5), $a_p^\dagger$, $a_q$ represent fermionic creation and annihilation operators, $n_p = a_p^\dagger a_p$ represents the number operator and $T_{l,pq}$, $V_{l,pq}$ represent scalar coefficients. The first term of Equation (5) represents a kinetic energy term (which may include an external potential term). The second term of Equation (5) represents an interaction term. Trotter steps under a fermionic Hamiltonian given by equation (5) may be efficiently implemented using known techniques, such as a linear array/linear depth procedure.

To decompose the electronic structure Hamiltonian given by Equation (1) into the sum of sub-Hamiltonians given by Equation (2), the system may first define an initial basis then use the defined initial basis to iteratively determine each sub-Hamiltonian in the sum of sub-Hamiltonians given by Equation (2). For example, for a first iteration, the system may identify a basis transformation $u_1$ that, when applied to the initial basis, defines a new basis for the iteration. The basis transformation $u_1$ may then be used to define a corresponding transformation operator $R(u_1)$ and the corresponding fermionic Hamiltonian $H(\vec{T}_1, \vec{V}_1) = \sum_{pq} T_{1,pq} a_p^\dagger a_q + \sum_{p \neq q} V_{1,pq} n_p n_q$.

For an l-th iteration, the system may identify a basis transformation $u_l$, that, when applied to the basis for the previous iteration, defines a new basis for the iteration. The identified basis transformation for the iteration may then be used to define a corresponding transformation operator $R(u_l)$ and corresponding fermionic Hamiltonian $H(\vec{T}_l, \vec{V}_l) = \sum_{pq} T_{l,pq} a_p^\dagger a_q + \sum_{p \neq q} V_{l,pq} n_p n_q$. The total number of iterations may depend on a predetermined target precision for the decomposition. In some cases, the system may determine a basis transformation $u_l$ as a basis transformation that minimizes the difference between the electronic structure Hamiltonian and a preliminary decomposition corresponding to previous iterations plus a best candidate current sub-Hamiltonian from a set of possible candidate current sub-Hamiltonians, e.g., $$\operatorname*{argmin}_{u_*} \left\| \tilde{H} - \sum_{j=1}^{l} R(u_j) H(\vec{T}_l, \vec{V}_l) R(u_j)^\dagger - R(u_*) H(\vec{T}_*, \vec{V}_*) R(u_*)^\dagger \right\|$$

One example process for defining a basis is described in detail below with reference to FIG. 4.

In some implementations the decomposed electronic structure Hamiltonian, e.g., as given by equation (2), may be equivalent to the electronic structure Hamiltonian, e.g., as given by equation (1). In other implementations the decomposed electronic structure Hamiltonian, e.g., as given by equation (2), may approximate the electronic structure Hamiltonian expressed in the orthonormal basis, e.g., as given by Equation (1). For example, in some implementations the sequence $u_1, u_2, \ldots, u_L$ may be truncated to some value L'<L so that the difference between the electronic structure Hamiltonian defined in Equation (1) and the truncated decomposed electronic structure Hamiltonian defined in Equation (2) is smaller than a predefined target precision, that is $$\left\| \tilde{H} - \sum_{l=1}^{L'} R(u_l) H(\vec{T}_l, \vec{V}_l) R(u_l)^\dagger \right\| \leq \epsilon$$

where $\epsilon$ represents the predefined target precision. In some implementations and depending on the particular structure of the electronic structure Hamiltonian given in Equation (1), truncating the sequence to a value L'<L may improve computational efficiency of the simulation process.

In some implementations, e.g., those where the sequence $u_1, u_2, \ldots, u_L$ is truncated to some value L'<L, many decompositions of the electronic structure Hamiltonian given by equation (1) may achieve a same precision $\epsilon$. In these implementations, the system may determine multiple candidate decompositions of the electronic structure Hamiltonian and select the candidate decomposition that is the most sparse, i.e., includes the fewest number of terms, as the decomposition to be used to simulate the physical system. Determining the most sparse decomposition may include applying matching pursuit or orthogonal matching pursuit techniques, as described below with reference to FIG. 3.

The system simulates evolution of the physical system using the decomposed electronic structure Hamiltonian (step 204). To simulate the evolution of the physical system the system may implement multiple Trotter steps under the decomposed Hamiltonian given by Equation (2) above. To implement a Trotter step, the system may define a unitary operator comprising a product of terms, each term corresponding to a respective identified basis for each iteration, each term comprising a product of i) the transformation operator effecting the basis transformation for the iteration, ii) a Trotter step under the fermionic Hamiltonian expressed in the basis for the iteration, and iii) the Hermitian conjugate of the transformation operator effecting the basis transformation for the iteration. For example, the unitary operator may be given by Equation (6) below.

$$\tilde{U} = \prod_{l=0}^{L-1} R(u_l) A(\vec{T}_l, \vec{V}_l) R(u_l)^\dagger \quad (6)$$

In Equation (6), $R(u_l)$ represents a transformation operator effecting the basis transformation for an l-th iteration and $A(\vec{T}_l, \vec{V}_l)$ represents a Trotter step under the fermionic Hamiltonian expressed in a basis defined via $u_l$. As described above, $A(\vec{T}_l, \vec{V}_l)$ can be determined using known techniques, such as a linear array/linear depth procedure.

In some implementations, implementing the Trotter step under the decomposed electronic structure Hamiltonian using the unitary operator defined in Equation (6) may include applying a quantum circuit effecting the unitary operator on a state of a corresponding quantum system, e.g., an initial state. The total depth of the quantum circuit is 2NL since the circuit depth of the basis change is N the circuit depth of the Trotter step under the fermionic Hamiltonian is N and because $R(u_l)^\dagger R(u_{l+1})$ can be expressed as a single rotation operation instead of two operations.

In other implementations, implementing the Trotter step under the decomposed electronic structure Hamiltonian using the unitary operator defined in Equation (6) may include simulating the Trotter step.

The system uses the simulated evolution of the physical system using the decomposed electronic structure Hamiltonian to determine properties of the physical system (step 206). For example, the process 200 may be used to determine properties of single molecules and simulate catalysts or pharmaceuticals, for performing material science simulations such as those required to understand the fractional quantum Hall effect or the Sachdev-Ye-Kitaev model, or for determining the rates of chemical reactions. As another example, the electronic structure Hamiltonian may characterize the electronic structure of a semiconductor. In these cases the system may use the simulated evolution of the physical system to simulate properties of the semiconductor, e.g., the conductivity or resistance of the semiconductor. Such simulation results may be used to fabricate semiconductor devices, e.g., integrated circuits.

Figure 3:
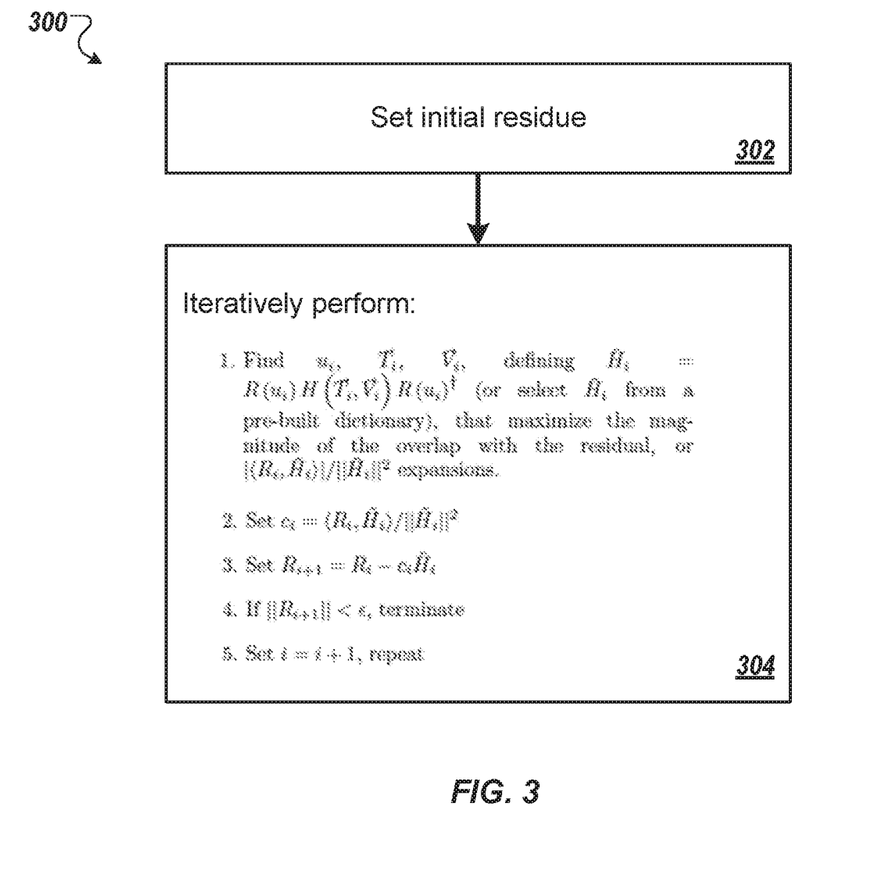
FIG. 3 is a flow diagram of an example process for decomposing an electronic structure Hamiltonian using a matching pursuit algorithm.

FIG. 3 is a flow diagram of an example process 300 for decomposing an electronic structure Hamiltonian using a matching pursuit algorithm. For convenience, the process 300 will be described as being performed by a system of one or more classical or quantum computing devices located in one or more locations. For example, a quantum computation system, e.g., the system 100 of FIG. 1, appropriately programmed in accordance with this specification, can perform the process 300.

The system sets an initial residue $R_{i=1}=H$ (step 302).

The system iteratively performs, until convergence tolerance $\|R_i\| < \epsilon$ for some chosen precision $\epsilon$, the following steps (step 304):

1) identify a basis rotation $u_i$ and scalar coefficients $T_i$, $V_i$ that define a sub-Hamiltonian $\widetilde{H}_i = R(u_i) H(\vec{T}_i, \vec{V}_i) R(u_i)^\dagger$ that maximizes the magnitude of the overlap with a residual for previous repetition. Alternatively, $\widetilde{H}_i$ may be selected from a pre-build dictionary.

2) set $c_i = \langle R_i \widetilde{H}_i \rangle / \|\widetilde{H}_i\|^2$ 3) set $R_{i+1} = c_i \widetilde{H}_i$ 4) determine whether $\|R_{i+1}\| < \epsilon$ 5) in response to determining that $\|R_{i+1}\| \geq \epsilon$, performing a further iteration 6) in response to determining that $\|R_{i+1}\| < \epsilon$, terminating the performing 7) at termination, setting the candidate decomposition as $\tilde{H} = \Sum_i^L c_i \widetilde{H}_i$ where L represents the total number of iterations.

This matching pursuit algorithm attempts to find the smallest expansion of the Hamiltonian, resulting in the lowest cost simulation algorithm. The above algorithm can be modified to perform orthogonal matching pursuit by solving an additional linear system within each iteration of the algorithm that re-optimizes the $c_i$ given all current atoms that have been selected. This step adds some additional cost and complexity, but can result in much shorter sequences.

The leading cost of the above described method for decomposition is the nonlinear optimization that is used to select the matching pursuit dictionary on the fly. This form of optimization is often better conditioned and faster to converge than the global optimization of all coefficients as above, moreover it can be used as a starting step to other more complex optimizations. Given the modest dimensionality of the space (polynomial as opposed to exponential), it is also possible to perform this decomposition without non-linear optimization, by pre-generating an overcomplete dictionary of possible $\widetilde{H}_i$. In this case, an exact decomposition is always possible and the number of pre-computed basis rotations can be better controlled, however the expansions may not be as compact. Such an approach is closer to the original forms of matching pursuit, which builds on a faster discrete optimization as opposed to non-linear forms. In addition, if a pre-optimized overcomplete dictionary is available, other techniques from compressive sensing utilizing convex L1 optimization can be used to build the decomposition.

Density Fitting Diagonalization

In order to deal with the two-body term in the Hamiltonian given above in Equation (1), density fitting can be applied to map the two-body terms to an auxiliary basis, and subsequently diagonalize it to create an effective one-body term.

Figure 4:
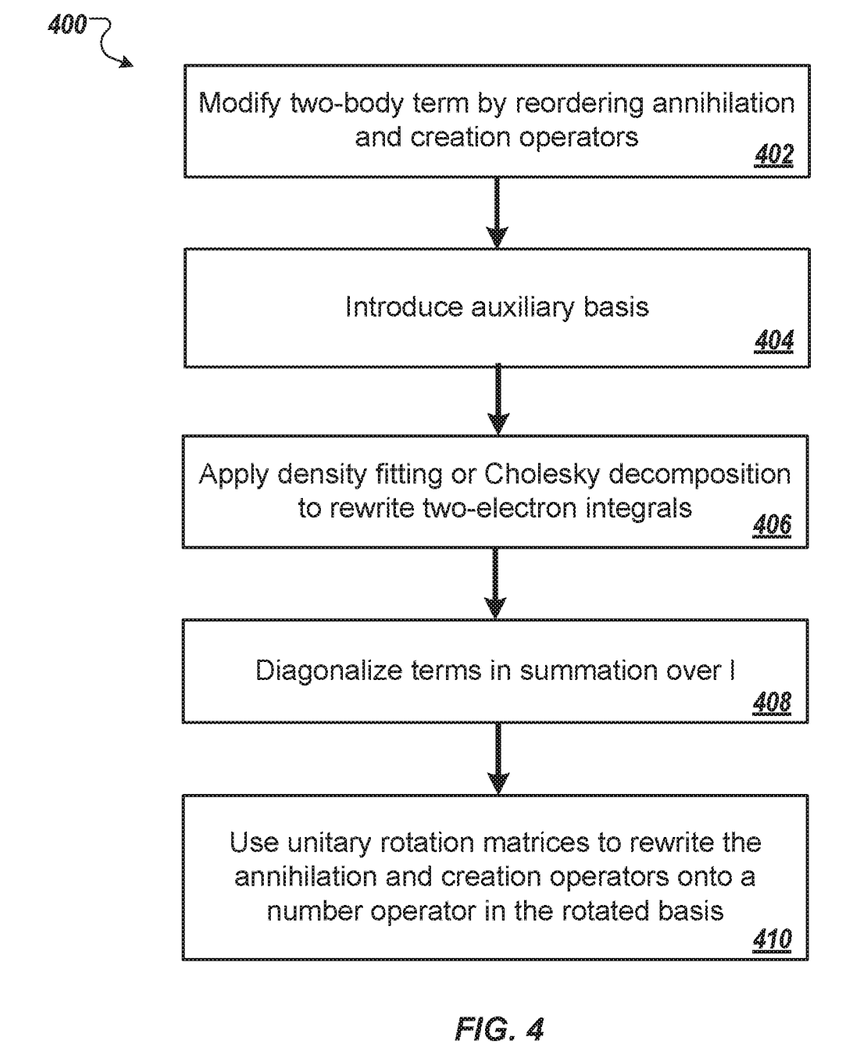
FIG. 4 is a flow diagram of an example density fitting process.

FIG. 4 is a flow diagram of an example density fitting process 400. For convenience, the process 300 will be described as being performed by a system of one or more classical or quantum computing devices located in one or more locations. For example, a quantum computation system, e.g., the system 100 of FIG. 1, appropriately programmed in accordance with this specification, can perform the process 400.

The system modifies the two-body term in Equation (1) above (step 402). To modify the two-body term, the system reorders the annihilation and creation operators as given below:

$$V = \frac{1}{2} \sum_{pqrs} (ps|qr) a_p^\dagger a_q^\dagger a_r a_s = \frac{1}{2} \sum_{pqrs} (ps|qr) a_p^\dagger a_r \delta_{qs} - a_p^\dagger a_s a_q^\dagger a_r$$

where (ps|qr) represents a (11|22) two-electron integral defined as $h_{pqrs} = \int (\phi_p^*(r_1) \phi_q^*(r_2) \phi_r(r_2) \phi_s(r_1) / |r_1 - r_2|) \, dr_1 dr_2$ with $\phi_s(r)$ represent basis functions. The system does not modify the one-body term of Equation (I) since this term involves a single annihilation and creation operation and can be simulated efficiently.

The system introduces an auxiliary basis $\chi$ onto which the two-electron system ps can be decomposed (step 404), as given below:

$$|ps\rangle = \sum_i d_i^{ps} \chi_i.$$

The system applies density fitting methods or a Cholesky decomposition to rewrite the two-electron integrals (step 406), as given below:

$$(ps|qr) = \sum_{ijl} (ps|i)\sqrt{(i|l)^{-1}} \sqrt{(l|j)^{-1}} (j|qr).$$

The system diagonalizes the terms in the summation over l (step 408), as given below:

$$\sum_i (ps|i)\sqrt{(i|j)^{-1}} = \sum_m [R(u_l)]_{mp} \lambda_m^{(l)} [R(u_l)]_{ms}.$$

The system uses the unitary rotation matrices $[R(u_l)]$ to rewrite the creation and annihilation operators into a number operator in the rotated basis (step 410), as given below:

$$n_m^{(l)} = \sum_{ps} [R(u_l)]_{mp} a_p^\dagger a_s [R(u_l)]_{ms}.$$

The two-body term may then be written as $$V = \sum_l R(u_l) \left( \frac{1}{2} \sum_{p \neq q} \lambda_p^{(l)} \lambda_q^{(l)} n_p n_q \right) R(u_l)^\dagger.$$

Using this change of basis, the Hamiltonian given by Equation (1) above may be written in terms of single-body operators, which can be simulated efficiently. Moreover, instead of naively summing over $M^4$ in the original basis, where M represents the number of atomic or molecular basis states used, the summation only contains order $M^3$ terms.

Implementations of the digital and/or quantum subject matter and the digital functional operations and quantum operations described in this specification can be implemented in digital electronic circuitry, suitable quantum circuitry or, more generally, quantum computational systems, in tangibly-embodied digital and/or quantum computer software or firmware, in digital and/or quantum computer hardware, including the structures disclosed in this specification and their structural equivalents, or in combinations of one or more of them. The term "quantum computational systems" may include, but is not limited to, quantum computers, quantum information processing systems, quantum cryptography systems, or quantum simulators.

Implementations of the digital and/or quantum subject matter described in this specification can be implemented as one or more digital and/or quantum computer programs, i.e., one or more modules of digital and/or quantum computer program instructions encoded on a tangible non-transitory storage medium for execution by, or to control the operation of, data processing apparatus. The digital and/or quantum computer storage medium can be a machine-readable storage device, a machine-readable storage substrate, a random or serial access memory device, one or more qubits, or a combination of one or more of them. Alternatively or in addition, the program instructions can be encoded on an artificially-generated propagated signal that is capable of encoding digital and/or quantum information, e.g., a machine-generated electrical, optical, or electromagnetic signal, that is generated to encode digital and/or quantum information for transmission to suitable receiver apparatus for execution by a data processing apparatus.

The terms quantum information and quantum data refer to information or data that is carried by, held or stored in quantum systems, where the smallest non-trivial system is a qubit, i.e., a system that defines the unit of quantum information. It is understood that the term "qubit" encompasses all quantum systems that may be suitably approximated as a two-level system in the corresponding context. Such quantum systems may include multi-level systems, e.g., with two or more levels. By way of example, such systems can include atoms, electrons, photons, ions or superconducting qubits. In many implementations the computational basis states are identified with the ground and first excited states, however it is understood that other setups where the computational states are identified with higher level excited states are possible.

The term "data processing apparatus" refers to digital and/or quantum data processing hardware and encompasses all kinds of apparatus, devices, and machines for processing digital and/or quantum data, including by way of example a programmable digital processor, a programmable quantum processor, a digital computer, a quantum computer, multiple digital and quantum processors or computers, and combinations thereof. The apparatus can also be, or further include, special purpose logic circuitry, e.g., an FPGA (field programmable gate array), an ASIC (application-specific integrated circuit), or a quantum simulator, i.e., a quantum data processing apparatus that is designed to simulate or produce information about a specific quantum system. In particular, a quantum simulator is a special purpose quantum computer that does not have the capability to perform universal quantum computation. The apparatus can optionally include, in addition to hardware, code that creates an execution environment for digital and/or quantum computer programs, e.g., code that constitutes processor firmware, a protocol stack, a database management system, an operating system, or a combination of one or more of them.

A digital computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a digital computing environment. A quantum computer program, which may also be referred to or described as a program, software, a software application, a module, a software module, a script, or code, can be written in any form of programming language, including compiled or interpreted languages, or declarative or procedural languages, and translated into a suitable quantum programming language, or can be written in a quantum programming language, e.g., QCL, or Quipper.

A digital and/or quantum computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A digital and/or quantum computer program can be deployed to be executed on one digital or one quantum computer or on multiple digital and/or quantum computers that are located at one site or distributed across multiple sites and interconnected by a digital and/or quantum data communication network. A quantum data communication network is understood to be a network that may transmit quantum data using quantum systems, e.g. qubits. Generally, a digital data communication network cannot transmit quantum data, however a quantum data communication network may transmit both quantum data and digital data.

The processes and logic flows described in this specification can be performed by one or more programmable digital and/or quantum computers, operating with one or more digital and/or quantum processors, as appropriate, executing one or more digital and/or quantum computer programs to perform functions by operating on input digital and quantum data and generating output. The processes and logic flows can also be performed by, and apparatus can also be implemented as, special purpose logic circuitry, e.g., an FPGA or an ASIC, or a quantum simulator, or by a combination of special purpose logic circuitry or quantum simulators and one or more programmed digital and/or quantum computers.

For a system of one or more digital and/or quantum computers to be "configured to" perform particular operations or actions means that the system has installed on it software, firmware, hardware, or a combination of them that in operation cause the system to perform the operations or actions. For one or more digital and/or quantum computer programs to be configured to perform particular operations or actions means that the one or more programs include instructions that, when executed by digital and/or quantum data processing apparatus, cause the apparatus to perform the operations or actions. A quantum computer may receive instructions from a digital computer that, when executed by the quantum computing apparatus, cause the apparatus to perform the operations or actions.

Digital and/or quantum computers suitable for the execution of a digital and/or quantum computer program can be based on general or special purpose digital and/or quantum processors or both, or any other kind of central digital and/or quantum processing unit. Generally, a central digital and/or quantum processing unit will receive instructions and digital and/or quantum data from a read-only memory, a random access memory, or quantum systems suitable for transmitting quantum data, e.g. photons; or combinations thereof.

The essential elements of a digital and/or quantum computer are a central processing unit for performing or executing instructions and one or more memory devices for storing instructions and digital and/or quantum data. The central processing unit and the memory can be supplemented by, or incorporated in, special purpose logic circuitry or quantum simulators, Generally, a digital and/or quantum computer will also include, or be operatively coupled to receive digital and/or quantum data from or transfer digital and/or quantum data to, or both, one or more mass storage devices for storing digital and/or quantum data, e.g., magnetic, magneto-optical disks, optical disks, or quantum systems suitable for storing quantum information. However, a digital and/or quantum computer need not have such devices.

Digital and/or quantum computer-readable media suitable for storing digital and/or quantum computer program instructions and digital and/or quantum data include all forms of non-volatile digital and/or quantum memory, media and memory devices, including by way of example semiconductor memory devices, e.g., EPROM, EEPROM, and flash memory devices; magnetic disks, e.g., internal hard disks or removable disks; magneto-optical disks; CD-ROM and DVD-ROM disks; and quantum systems, e.g., trapped atoms or electrons. It is understood that quantum memories are devices that can store quantum data for a long time with high fidelity and efficiency, e.g., light-matter interfaces where light is used for transmission and matter for storing and preserving the quantum features of quantum data such as superposition or quantum coherence.

Control of the various systems described in this specification, or portions of them, can be implemented in a digital and/or quantum computer program product that includes instructions that are stored on one or more non-transitory machine-readable storage media, and that are executable on one or more digital and/or quantum processing devices. The systems described in this specification, or portions of them, can each be implemented as an apparatus, method, or system that may include one or more digital and/or quantum processing devices and memory to store executable instructions to perform the operations described in this specification.

While this specification contains many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A method for simulating a physical system described by an electronic structure Hamiltonian expressed in an orthonormal basis, the method implemented by a system comprising a classical processor and quantum hardware, wherein the quantum hardware comprises a plurality of connected qubits and a plurality of control devices configured to apply quantum logic gates to the plurality of connected qubits, the method comprising:

decomposing, by the classical processor, the electronic structure Hamiltonian into a sum of sub-Hamiltonians, wherein each sub-Hamiltonian in the sum of sub-Hamiltonians:
is expressed in a respective basis of multiple different bases of the other sub-Hamiltonians in the sum of sub-Hamiltonians; and
comprises the product of i) a transformation operator effecting a respective basis rotation from an initial basis to the one basis of the multiple different bases, ii) a fermionic Hamiltonian expressed in the respective basis, the fermionic Hamiltonian comprising $O(N^2)$ terms with N representing system size, and iii) a Hermitian conjugate of the transformation operator effecting the respective basis rotation from the initial basis to the one basis of the multiple different bases, wherein the transformation operator and fermionic Hamiltonian comprise fermionic creation and annihilation operators;
simulating, using the quantum hardware, evolution of the physical system using the decomposed electronic structure Hamiltonian, comprising, for each sub-Hamiltonian that is expressed in a respective basis of the multiple different bases, applying a respective quantum circuit of quantum logic gates to an initial state of the plurality of qubits to implement a Trotter step of unitary evolution in the respective basis of the multiple different bases, wherein the quantum circuit requires linear qubit connectivity and has a depth that is linear in the system size; and
using, by the classical processor, the simulated evolution of the physical system using the decomposed electronic structure Hamiltonian to determine properties of the physical system.

2. The method of claim 1, wherein the physical system comprises a periodic physical system or a non-periodic physical system.

3. The method of claim 1, wherein the orthonormal basis comprises a Gaussian or general molecular orbital basis.

4. The method of claim 1, wherein the electronic structure Hamiltonian expressed in the orthonormal basis and the decomposed electronic structure Hamiltonian expressed in multiple bases are equivalent.

5. The method of claim 1, wherein the decomposed electronic structure Hamiltonian expressed in multiple bases approximates the electronic structure Hamiltonian expressed in the orthonormal basis.

6. The method claim 1, wherein the fermionic Hamiltonian comprises a kinetic energy term and an interaction term.

7. The method of claim 6, wherein the fermionic Hamiltonian is given by $$H(\vec{T}_l, \vec{V}_l) = \sum_{pq} T_{l,pq} a_p^\dagger a_q + \sum_{p \neq q} V_{l,pq} n_p n_q$$

where $a_p^\dagger$, $a_q$ represent fermionic creation and annihilation operators, $n_p = a_p^\dagger a_p$ represents the number operator and $T_{l,pq}$, $V_{l,pq}$ represent scalar coefficients.

8. The method of claim 1, wherein Trotter steps under the fermionic Hamiltonian are implemented using a linear array or linear depth procedure.

9. The method of claim 1, wherein decomposing the electronic structure Hamiltonian into a sum of sub-Hamiltonians comprises:
defining an initial basis; and
iteratively determining each sub-Hamiltonian in the sum of sub-Hamiltonians, comprising for each iteration:
identifying a basis transformation that defines a basis for the iteration;
determining i) a transformation operator effecting the identified basis transformation, and ii) the fermionic Hamiltonian expressed in the basis for the iteration.

10. The method of claim 1, wherein decomposing the electronic structure Hamiltonian into a sum of sub-Hamiltonians comprises:
determining multiple candidate decompositions of the electronic structure Hamiltonian; and
selecting a candidate decomposition comprising the fewest number of sub-Hamiltonians as the decomposition.

11. The method of claim 10, wherein selecting a candidate decomposition comprising the fewest number of sub-Hamiltonians as the decomposition comprises applying a matching pursuit algorithm.

12. The method of claim 11, wherein applying a matching pursuit algorithm comprises:
set an initial residue;
iteratively performing, until a termination criterion is satisfied, steps comprising:
identifying a basis rotation u; and scalar coefficients $T_i$, $V_i$ that define a sub-Hamiltonian $R(u_i) H(\vec{T}_i, \vec{V}_i) R(u_i)^\dagger$ that maximizes the magnitude of the overlap with a residual for previous repetition;
calculate a constant $c_i = \langle R_i \widetilde{H}_\iota \rangle / \|\widetilde{H}_\iota\|^2$
set $R_{i+1} = R_i - c_i \widetilde{H}_\iota$;
determine whether $\|R_{i+1}\| < \epsilon$;
in response to determining that $\|R_{i+1}\| \geq \epsilon$, performing a further iteration;
in response to determining that $\|R_{i+1}\| < \epsilon$, terminating the performing; and
setting the candidate composition as $\tilde{H} = \Sigma_i^L c_i \widetilde{H}_\iota$ where L represents the total number of iterations.

13. The method of claim 12, further comprising performing an orthogonal matching pursuit algorithm by solving an additional linear system in each iteration that optimizes the constant $c_i$ given all current selected atoms.

14. The method of claim 1, wherein simulating evolution of the physical system using the decomposed electronic structure Hamiltonian comprises:
implementing a Trotter step using a unitary operator defined as a product of terms, each term corresponding to a respective identified basis for each iteration, each term comprising a product of i) the transformation operator effecting the basis transformation for the iteration, ii) a Trotter step under the fermionic Hamiltonian expressed in the basis for the iteration, and iii) the Hermitian conjugate of the transformation operator effecting the basis transformation for the iteration.

15. The method of claim 14, wherein implementing the Trotter step using the unitary operator comprises applying a quantum circuit effecting the unitary operator on a state of a quantum system.

16. The method of claim 14, wherein implementing the Trotter step using the unitary operator comprises simulating the Trotter step.

17. The method of claim 1, wherein the electronic structure Hamiltonian expressed in the orthonormal basis characterizes the electronic structure of a semiconductor, and wherein using the simulated evolution of the physical system using the decomposed electronic structure Hamiltonian to determine properties of the physical system comprises determining properties of the semiconductor.

18. The method of claim 17, wherein properties of the semiconductor comprise conductivity or resistance.

19. An apparatus comprising:
quantum hardware comprising a plurality of connected qubits and a plurality of control devices configured to apply quantum logic gates to the plurality of connected qubits; and
one or more classical processors;
wherein the apparatus is configured to simulate a physical system described by an electronic structure Hamiltonian expressed in an orthonormal basis by performing operations comprising:
 decomposing, by the classical processor, the electronic structure Hamiltonian into a sum of sub-Hamiltonians, wherein each sub-Hamiltonian in the sum of sub-Hamiltonians:
  is expressed in a respective basis of multiple different bases of the other sub-Hamiltonians in the sum of sub-Hamiltonians; and
  comprises the product of i) a transformation operator effecting a respective basis rotation from an initial basis to the one basis of the multiple different bases, ii) a fermionic Hamiltonian expressed in the respective basis, the fermionic Hamiltonian comprising $O(N^2)$ terms with N representing system size, and iii) a Hermitian conjugate of the transformation operator effecting the respective basis rotation from the initial basis to the one basis of the multiple different bases, wherein the transformation operator and fermionic Hamiltonian comprise fermionic creation and annihilation operators;
 simulating, using the quantum hardware, evolution of the physical system using the decomposed electronic structure Hamiltonian, comprising, for each sub-Hamiltonian that is expressed in a respective basis of the multiple different bases, applying a respective quantum circuit of quantum logic gates to an initial state of the plurality of qubits to implement a Trotter step of unitary evolution in the respective basis of the multiple different bases, wherein the quantum circuit requires linear qubit connectivity and has a depth that is linear in the system size; and
using, by the classical processor, the simulated evolution of the physical system using the decomposed electronic structure Hamiltonian to determine properties of the physical system.

* * * * *